(12) United States Patent
Qiu

(10) Patent No.: US 9,359,429 B2
(45) Date of Patent: Jun. 7, 2016

(54) ANTI-CYANOBACTERIA RECOMBINANT ANTIBODY POLYPEPTIDE, GENE THEREOF, AND PREPARATION METHOD THEREOF

(75) Inventor: Xiaoqing Qiu, Beijing (CN)

(73) Assignee: Protein Design Lab, Ltd., Beijing (CN)

( * ) Notice: Subject to any disclaimer, the term of this patent is extended or adjusted under 35 U.S.C. 154(b) by 68 days.

(21) Appl. No.: 14/113,188

(22) PCT Filed: Mar. 27, 2012

(86) PCT No.: PCT/CN2012/073120
§ 371 (c)(1),
(2), (4) Date: Jan. 9, 2014

(87) PCT Pub. No.: WO2012/142899
PCT Pub. Date: Oct. 26, 2012

(65) Prior Publication Data
US 2014/0170170 A1     Jun. 19, 2014

(30) Foreign Application Priority Data

Apr. 21, 2011  (CN) .......................... 2011 1 0100775
Jun. 10, 2011  (CN) .......................... 2011 1 0155221

(51) Int. Cl.
| | |
|---|---|
| *A61K 39/40* | (2006.01) |
| *A61K 39/00* | (2006.01) |
| *A61K 39/395* | (2006.01) |
| *C07K 16/14* | (2006.01) |
| *C02F 1/50* | (2006.01) |
| *C07K 16/12* | (2006.01) |
| *C12N 5/16* | (2006.01) |

(52) U.S. Cl.
CPC ................. *C07K 16/14* (2013.01); *A61K 39/00* (2013.01); *C02F 1/50* (2013.01); *C07K 16/12* (2013.01); *C12N 5/163* (2013.01)

(58) Field of Classification Search
CPC ..... A61K 39/00; A61K 39/02; A61K 39/395; A61K 39/40
USPC .......... 424/130.1, 141.1, 150.1, 164.1, 178.1
See application file for complete search history.

(56) References Cited

FOREIGN PATENT DOCUMENTS

| | | | |
|---|---|---|---|
| CN | 101633699 | 1/2010 | |
| JP | 7089998 A | 4/1995 | |
| JP | H1057055 A | * 3/1998 | ............. C12N 15/02 |
| WO | WO-2013/083095 | 6/2013 | |

OTHER PUBLICATIONS

Database Accession No. BAP67929, "Antibiotic biotic preparation-related antibody mimetic peptide, SEQ:27," dated Aug. 1, 2013, retrieved on Sep. 11, 2014, from DGENE on STN, 1 page.

Extended European Search Report in EP12773570.2, dated Sep. 2014, 6 pages.

International Preliminary Report on Patentability and Written Opinion for PCT/CN2012/073120, dated Oct. 22, 2013, 11 pages (translation included).

International Search Report for PCT/CN2012/073120, mailed Jun. 28, 2012, 14 pages (translation included).

Rennis, "Differences in antigenic reactivity of six types of phycoerythrin to monoclonal anti-R-phycoerythrin", Phycologia (1991) 30(4):329-338.

* cited by examiner

*Primary Examiner* — Rodney P Swartz
(74) *Attorney, Agent, or Firm* — Morrison & Foerster LLP

(57) ABSTRACT

Provided are a hybridoma cell CGMCC No. 4783 that secretes a monoclonal antibody of an anti-cyanobacteria cell surface antigen, and the secreted monoclonal antibody thereof. Also provided are an anti-cyanobacteria recombinant antibody polypeptide, encoding gene, preparation method and use thereof. The anti-cyanobacteria recombinant antibody polypeptide is composed of an anti-cyanobacteria antibody mimetic polypeptide operably linearly connecting to the carboxyl terminal of an *Escherichia coli* polypeptide. The anti-cyanobacteria antibody mimetic polypeptide is a polypeptide with cyanobacteria identifying and binding capability designed based on an antigen binding fragment of the monoclonal antibody secreted by the CGMCC No. 4783 hybridoma cell. The anti-cyanobacteria recombinant antibody polypeptide directly form an ion channel on the cell membrane of a cyanobacteria to kill the cyanobacteria, targeted killing the cyanobacteria (prokaryote) without killing other beneficial eukaryotic cell algae.

14 Claims, 11 Drawing Sheets

Figure 1:
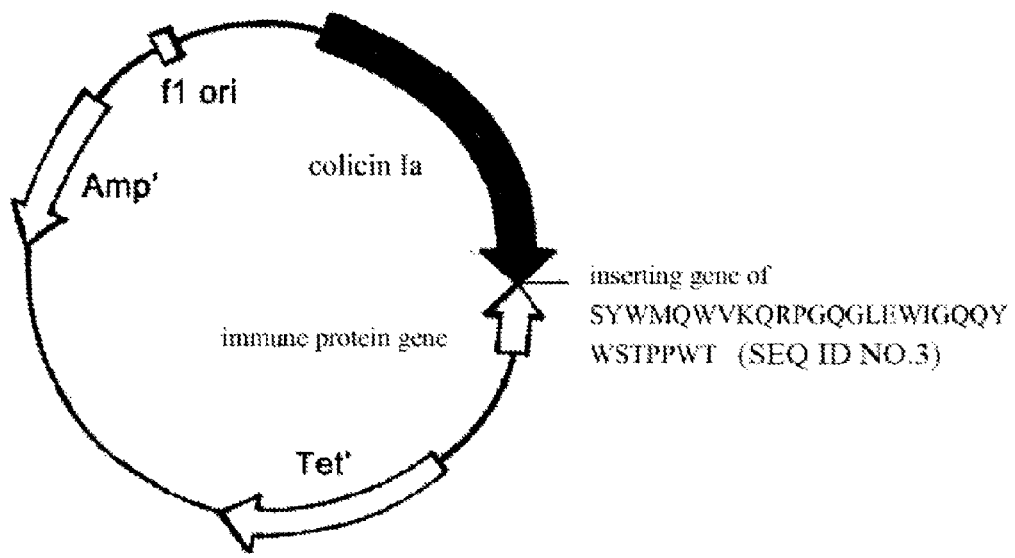

SEQUENCE LISTING

```
<160> NUMBER OF SEQ ID NOS: 15

<210> SEQ ID NO 1
<211> LENGTH: 1878
<212> TYPE: DNA
<213> ORGANISM: Artificial Sequence
<220> FEATURE:
<223> OTHER INFORMATION: synthetic construct encoding colicin Ia

<400> SEQUENCE: 1
atgtctgacc ctgtacgtat tacaaatccc ggtgcagaat cgctggggta tgattcagat      60
ggccatgaaa ttatggccgt tgatatttat gtaaaccctc cacgtgtcga tgtctttcat     120 ggtacccgc ctgcatggag ttccttcggg aacaaaacca tctggggcgg aaacgagtgg     180
gttgatgatt ccccaacccg aagtgatatc gaaaaaaggg acaaggaaat cacagcgtac     240
aaaaacacgc tcagcgcgca gcagaaagag aatgagaata gcgtactga agccggaaaa     300 cgcctctctg cggcgattgc tgcaagggaa aaagatgaaa cacactgaa acactccgt     360 gccggaaacg cagatgccgc tgatattaca cgacaggagt tcagactcct gcaggcagag     420
ctgagagaat acgattccg tactgaaatc gccggatatg acgccctccg gctgcataca     480
gagagccgga tgctgtttgc tgatgctgat tctcttcgta tatctccccg ggaggccagg     540
tcgttaatcg aacaggctga aaacggcag aaggatgcgc agaacgcaga caagaaggcc     600
gctgatatgc ttgctgaata cgagcgcaga aaaggtattc tggacacccg gttgtcagag     660
```

```
ctggaaaaaa atggcggggc agcccttgcc gttcttgatg cacaacaggc ccgtctgctc    720
gggcagcaga cacggaatga cagggccatt tcagaggccc ggaataaaact cagttcagtg    780 acggaatcgc ttaacacggc ccgtaatgca ttaaccagag ctgaacaaca gctgacgcaa    840
cagaaaaaca cgcctgacgg caaaacgata gtttcccctg aaaaattccc ggggcgttca    900
tcaacaaatc attctattgt tgtgagcggt gatccgagat ttgccggtac gataaaaatc    960
acaaccagcg cagtcatcga taaccgtgca aacctgaatt atcttctgag ccattccggt   1020
ctggactata aacgcaatat tctgaatgac cggaatccgg tggtgacaga ggatgtggaa   1080
ggtgacaaga aaatttataa tgctgaagtt gctgaatggg ataagttacg gcaaagattg   1140
cttgatgcca gaaataaaat cacctctgct gaatctgcgg taaattcggc gagaaataac   1200
ctcagtgcca gaacaaatga gcaaaagcat gcaaatgacg ctcttaatgc cctgttgaag   1260 gaaaagaga atatacgtaa ccagctttcc ggcatcaatc agaagatagc ggaagagaaa   1320
agaaaacagg atgaactgaa ggcaacgaaa gacgcaatta atttcacaac agagttcctg   1380
aaatcagttt cagaaaaata tggtgcaaaa gctgagcagt tagccagaga gatggccggg   1440
caggctaaag ggaagaaaat acgtaatgtt gaagaggcat taaaaacgta tgaaaagtac   1500
cgggctgaca ttaacaaaaa aattaatgca aaagatcgtg cagcgattgc cgcagcccttt  1560 gagtctgtga agctgtctga tatatcgtct aatctgaaca gattcagtcg gggactggga   1620
tatgcaggaa aatttacaag tcttgctgac tggatcactg agtttggtaa ggctgtccgg   1680
acagagaact ggcgtcctct ttttgttaaa acagaaacca tcatagcagg caatgccgca   1740
acggctcttg tggcactggt cttcagtatt cttaccggaa gcgctttagg cattatcggg   1800
tatggtttac tgatggctgt caccggtgcg ctgattgatg aatcgcttgt ggaaaaagcg   1860
aataagttct ggggtatt                                                1878

<210> SEQ ID NO 2
<211> LENGTH: 87
<212> TYPE: DNA
<213> ORGANISM: Artificial Sequence
<220> FEATURE:
<223> OTHER INFORMATION: synthetic construct of antibody mimetics
      against Microcystis aeruginosa surface antigen

<400> SEQUENCE: 2
tcttattgga tgcagtgggt taagcaaaga ccggggcaag ggctggagtg gattggccag    60
cagtattggt ctacgccgcc gtggacg                                        87

<210> SEQ ID NO 3
<211> LENGTH: 29
<212> TYPE: PRT
<213> ORGANISM: Artificial Sequence
<220> FEATURE:
<223> OTHER INFORMATION: synthetic construct of antibody mimetics
      against Microcystis aeruginosa surface antigen

<400> SEQUENCE: 3

Ser Tyr Trp Met Gln Trp Val Lys Gln Arg Pro Gly Gln Gly Leu Glu
1               5                   10                  15

Trp Ile Gly Gln Gln Tyr Trp Ser Thr Pro Pro Trp Thr
            20                  25

<210> SEQ ID NO 4
<211> LENGTH: 87
<212> TYPE: DNA
<213> ORGANISM: Artificial Sequence
```

<220> FEATURE:
<223> OTHER INFORMATION: synthetic construct VHCDR1 N-C in reversed order of gene of antibody mimetics against Microcystis aeruginosa surface antigen

<400> SEQUENCE: 4

```
cagatgtggt attcttgggt taagcaaaga ccggggcaag ggctggagtg gattggccag    60
cagtattggt ctacgccgcc gtggacg                                        87
```

<210> SEQ ID NO 5
<211> LENGTH: 29
<212> TYPE: PRT
<213> ORGANISM: Artificial Sequence
<220> FEATURE:
<223> OTHER INFORMATION: synthetic construct VHCDR1 N-C in reversed order of gene of antibody mimetics against Microcystis aeruginosa surface antigen

<400> SEQUENCE: 5

```
Gln Met Trp Tyr Ser Trp Val Lys Gln Arg Pro Gly Gln Gly Leu Glu
 1               5                  10                  15

Trp Ile Gly Gln Gln Tyr Trp Ser Thr Pro Pro Trp Thr
            20                  25
```

<210> SEQ ID NO 6
<211> LENGTH: 1965
<212> TYPE: DNA
<213> ORGANISM: Artificial Sequence
<220> FEATURE:
<223> OTHER INFORMATION: synthetic construct encoding anti-cyanobacteria polypeptide 1

<400> SEQUENCE: 6

```
atgtctgacc ctgtacgtat tacaaatccc ggtgcagaat cgctggggta tgattcagat    60
ggccatgaaa ttatggccgt tgatatttat gtaaaccctc cacgtgtcga tgtctttcat   120
ggtaccccgc ctgcatggag ttccttcggg aacaaaacca tctggggcgg aaacgagtgg   180
gttgatgatt ccccaacccg aagtgatatc gaaaaaggg acaaggaaat cacagcgtac    240
aaaaacacgc tcagcgcgca gcagaaagag aatgagaata gcgtactga agccggaaaa    300 cgcctctctg cggcgattgc tgcaagggaa aaagatgaaa acacactgaa acactccgt    360 gccggaaacg cagatgccgc tgatattaca cgacaggagt tcagactcct gcaggcagag    420
ctgagagaat acggattccg tactgaaatc gccggatatg acgccctccg gctgcataca    480
gagagccgga tgctgttgc tgatgctgat tctcttcgta tatctccccg ggaggccagg    540
tcgttaatcg aacaggctga aaacggcag aaggatgcgc agaacgcaga caagaaggcc    600
gctgatatgc ttgctgaata cgagcgcaga aaagtattc tggacacccg gttgtcagag    660
ctggaaaaaa atggcggggc agcccttgcc gttcttgatg cacaacaggc ccgtctgctc    720
gggcagcaga cacggaatga cagggccatt tcagaggccc ggaataaact cagttcagtg    780
acggaatcgc ttaacacggc ccgtaatgca ttaaccagag ctgaacaaca gctgacgcaa    840
cagaaaaaca cgcctgacgg caaaacgata gtttccctg aaaaattccc ggggcgttca    900
tcaacaaatc attctattgt tgtgagcggt gatccgagat tgccggtac gataaaaatc    960 acaaccagcg cagtcatcga taaccgtgca aacctgaatt atcttctgag ccattccggt   1020
ctggactata aacgcaatat tctgaatgac cggaatccgg tggtgacaga ggatgtggaa   1080
ggtgacaaga aaatttataa tgctgaagtt gctgaatggg ataagttacg gcaaagattg   1140
cttgatgcca gaaataaaat cacctctgct gaatctgcgg taaattcggc gagaaataac   1200
```

```
ctcagtgcca gaacaaatga gcaaaagcat gcaaatgacg ctcttaatgc cctgttgaag    1260 gaaaagaga atatacgtaa ccagctttcc ggcatcaatc agaagatagc ggaagagaaa    1320
agaaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aaagatcgtg cagcgattgc cgcagcccTT    1560
gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtatttc ttattggatg cagtgggtta agcaaagacc ggggcaaggg    1920
ctggagtgga ttggccagca gtattggtct acgccgccgt ggacg                  1965
```

<210> SEQ ID NO 7
<211> LENGTH: 654
<212> TYPE: PRT
<213> ORGANISM: Artificial Sequence
<220> FEATURE:
<223> OTHER INFORMATION: synthetic construct of anti-cyanobacteria

```
Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
            245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
            325                 330                 335

His Ser Gly Leu Asp Tyr Lys Arg Asn Ile Leu Asn Asp Arg Asn Pro
        340                 345                 350

Val Val Thr Glu Asp Val Glu Gly Asp Lys Lys Ile Tyr Asn Ala Glu
        355                 360                 365

Val Ala Glu Trp Asp Lys Leu Arg Gln Arg Leu Leu Asp Ala Arg Asn
370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
            405                 410                 415

Leu Leu Lys Glu Lys Glu Asn Ile Arg Asn Gln Leu Ser Gly Ile Asn
            420                 425                 430

Gln Lys Ile Ala Glu Gly Lys Arg Lys Gln Asp Glu Leu Lys Ala Thr
        435                 440                 445

Lys Asp Ala Ile Asn Phe Thr Thr Glu Phe Leu Lys Ser Val Ser Glu
        450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
            485                 490                 495

Glu Lys Tyr Arg Ala Asp Ile Asn Lys Lys Ile Asn Ala Lys Asp Arg
            500                 505                 510

Ala Ala Ile Ala Ala Ala Leu Glu Ser Val Lys Leu Ser Asp Ile Ser
        515                 520                 525

Ser Asn Leu Asn Arg Phe Ser Arg Gly Leu Gly Tyr Ala Gly Lys Phe
        530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
            565                 570                 575

Asn Ala Ala Thr Ala Leu Val Ala Leu Val Phe Ser Ile Leu Thr Gly
            580                 585                 590

Ser Ala Leu Gly Ile Ile Gly Tyr Gly Leu Leu Met Ala Val Thr Gly
        595                 600                 605

Ala Leu Ile Asp Glu Ser Leu Val Glu Lys Ala Asn Lys Phe Trp Gly
        610                 615                 620

Ile Ser Tyr Trp Met Gln Trp Val Lys Gln Arg Pro Gly Gln Gly Leu
625                 630                 635                 640
```

Glu Trp Ile Gly Gln Gln Tyr Trp Ser Thr Pro Pro Trp Thr
                    645                    650

<210> SEQ ID NO 8
<211> LENGTH: 1965
<212> TYPE: DNA
<213> ORGANISM: Artificial Sequence
<220> FEATURE:
<223> OTHER INFORMATION: synthetic construct encoding antifugal
     polypeptide 2

<400> SEQUENCE: 8

```
atgtctgacc ctgtacgtat tacaaatccc ggtgcagaat cgctggggta tgattcagat      60
ggccatgaaa ttatggccgt tgatatttat gtaaaccctc acgtgtcga tgtctttcat     120
ggtaccccgc ctgcatggag ttccttcggg aacaaaacca tctggggcgg aaacgagtgg    180
gttgatgatt ccccaacccg aagtgatatc gaaaaaggg acaaggaaat cacagcgtac     240
aaaaacacgc tcagcgcgca gcagaaagag aatgagaata gcgtactga agccggaaaa     300
cgcctctctg cggcgattgc tgcaaggaa aagatgaaa cacactgaa acactccgt        360
gccggaaacg cagatgccgc tgatattaca cgacaggagt tcagactcct gcaggcagag    420
ctgagagaat acggattccg tactgaaatc gccggatatg acgccctccg gctgcataca    480
gagagccgga tgctgtttgc tgatgctgat tctcttcgta tatctccccg ggaggccagg    540
tcgttaatcg aacaggctga aaacggcag aggatgcgc agaacgcaga caagaaggcc      600
gctgatatgc ttgctgaata cgagcgcaga aaaggtattc tggacacccg ttgtcagag     660
ctggaaaaaa atggcggggc agcccttgcc gttcttgatg cacaacaggc ccgtctgctc    720
gggcagcaga cacggaatga cagggccatt tcagaggccc ggaataaact cagttcagtg    780
acggaatcgc ttaacacggc ccgtaatgca ttaaccagag ctgaacaaca gctgacgcaa    840
cagaaaaaca cgcctgacgg caaaacgata gtttcccctg aaaattccc ggggcgttca     900
tcaacaaatc attctattgt tgtgagcggt gatccgagat ttgccggtac gataaaaatc    960
acaaccagcg cagtcatcga taaccgtgca aacctgaatt atcttctgag ccattccggt   1020
ctggactata aacgcaatat tctgaatgac cggaatccgg tggtgacaga ggatgtggaa   1080
ggtgacaaga aaatttataa tgcctgaagtt gctgaatggg ataagttacg gcaaagattg   1140
cttgatgcca gaaataaaat cacctctgct gaatctgcgg taaattcggc gagaaataac   1200
ctcagtgcca gaacaaatga gcaaaagcat gcaaatgacg ctcttaatgc cctgttgaag   1260
gaaaaagaga atatacgtaa ccagctttcc ggcatcaatc agaagatagc ggaagagaaa   1320
agaaaacagg atgaactgaa ggcaacgaaa gacgcaatta atttcacaac agagttcctg   1380
aaatcagttt cagaaaaata tggtgcaaaa gctgagcagt tagccagaga gatgccggg    1440
caggctaaag ggaagaaaat acgtaatgtt gaagaggcat taaaaacgta tgaaaagtac   1500
cgggctgaca ttaacaaaaa aattaatgca aagatcgtg cagcgattgc cgcagcccctt   1560
gagtctgtga agctgtctga tatatcgtct aatctgaaca gattcagtcg gggactggga   1620
tatgcaggaa aatttacaag tcttgctgac tggatcactg agtttggtaa ggctgtccgg   1680
acagagaact ggcgtcctct ttttgttaaa acagaaacca tcatagcagg caatgccgca   1740
acggctcttg tggcactggt cttcagtatt cttaccggaa gcgctttagg cattatcggg   1800
tatggtttac tgatggctgt caccggtgcg ctgattgatg aatcgcttgt ggaaaaagcg   1860
aataagttct ggggtattca gatgtggtat tcttgggtta agcaaagacc ggggcaaggg   1920
ctggagtgga ttggccagca gtattggtct acgccgccgt ggacg                    1965
```

-continued

```
<210> SEQ ID NO 9
<211> LENGTH: 654
<212> TYPE: PRT
<213> ORGANISM: Artificial Sequence
<220> FEATURE:
<223> OTHER INFORMATION: synthetic construct encoding antifugal
      polypeptide 2

<400> SEQUENCE: 9

Ser Asp Pro Val Arg Ile Thr Asn Pro Gly Ala Glu Ser Leu Gly Tyr
1               5                   10                  15

Asp Ser Asp Gly His Glu Ile Met Ala Val Asp Ile Tyr Val Asn Pro
            20                  25                  30

Pro Arg Val Asp Val Phe His Gly Thr Pro Pro Ala Trp Ser Ser Phe
        35                  40                  45

Gly Asn Lys Thr Ile Trp Gly Gly Asn Glu Trp Val Asp Asp Ser Pro
    50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
    130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
    290                 295                 300

Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
                325                 330                 335

His Ser Gly Leu Asp Tyr Lys Arg Asn Ile Leu Asn Asp Arg Asn Pro
            340                 345                 350

Val Val Thr Glu Asp Val Glu Gly Asp Lys Lys Ile Tyr Asn Ala Glu
```

```
                355                 360                 365
Val Ala Glu Trp Asp Lys Leu Arg Gln Arg Leu Leu Asp Ala Arg Asn
370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
                405                 410                 415

Leu Leu Lys Glu Lys Glu Asn Ile Arg Asn Gln Leu Ser Gly Ile Asn
                420                 425                 430

Gln Lys Ile Ala Glu Glu Lys Arg Lys Gln Asp Glu Leu Lys Ala Thr
                435                 440                 445

Lys Asp Ala Ile Asn Phe Thr Thr Glu Phe Leu Lys Ser Val Ser Glu
450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
                485                 490                 495

Glu Lys Tyr Arg Ala Asp Ile Asn Lys Lys Ile Asn Ala Lys Asp Arg
                500                 505                 510

Ala Ala Ile Ala Ala Ala Leu Glu Ser Val Lys Leu Ser Asp Ile Ser
                515                 520                 525

Ser Asn Leu Asn Arg Phe Ser Arg Gly Leu Gly Tyr Ala Gly Lys Phe
530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
                565                 570                 575

Asn Ala Ala Thr Ala Leu Val Ala Leu Val Phe Ser Ile Leu Thr Gly
                580                 585                 590

Ser Ala Leu Gly Ile Ile Gly Tyr Gly Leu Leu Met Ala Val Thr Gly
                595                 600                 605

Ala Leu Ile Asp Glu Ser Leu Val Glu Lys Ala Asn Lys Phe Trp Gly
                610                 615                 620

Ile Gln Met Trp Tyr Ser Trp Val Lys Gln Arg Pro Gly Gln Gly Leu
625                 630                 635                 640

Glu Trp Ile Gly Gln Gln Tyr Trp Ser Thr Pro Pro Trp Thr
                645                 650

<210> SEQ ID NO 10
<211> LENGTH: 69
<212> TYPE: DNA
<213> ORGANISM: Artificial Sequence
<220> FEATURE:
<223> OTHER INFORMATION: Synthetic Construct

<400> SEQUENCE: 10
gcgaataagt tctggggtat ttcttattgg atgcagtggg ttaagcaata aataaaatat    60
aagacaggc                                                           69

<210> SEQ ID NO 11
<211> LENGTH: 69
<212> TYPE: DNA
<213> ORGANISM: Artificial Sequence
<220> FEATURE:
<223> OTHER INFORMATION: Synthetic Construct

<400> SEQUENCE: 11
```

```
cgcttattca agaccccata aagaataacc tacgtcaccc aattcgttat ttattttata      60
ttctgtccg                                                             69

<210> SEQ ID NO 12
<211> LENGTH: 75
<212> TYPE: DNA
<213> ORGANISM: Artificial Sequence
<220> FEATURE:
<223> OTHER INFORMATION: Synthetic Construct

<400> SEQUENCE: 12
tattggatgc agtgggttaa gcaaagaccg gggcaagggc tggagtggat tggctaaata      60
aaatataaga caggc                                                      75

<210> SEQ ID NO 13
<211> LENGTH: 75
<212> TYPE: DNA
<213> ORGANISM: Artificial Sequence
<220> FEATURE:
<223> OTHER INFORMATION: Synthetic Construct

<400> SEQUENCE: 13
ataacctacg tcacccaatt cgtttctggc cccgttcccg acctcaccta accgatttat      60
tttatattct gtccg                                                      75

<210> SEQ ID NO 14
<211> LENGTH: 75
<212> TYPE: DNA
<213> ORGANISM: Artificial Sequence
<220> FEATURE:
<223> OTHER INFORMATION: Synthetic Construct

<400> SEQUENCE: 14
gggcaagggc tggagtggat tggccagcag tatyggtcta cgcccccgtg gacgtaaata      60
aaatataaga caggc                                                      75

<210> SEQ ID NO 15
<211> LENGTH: 75
<212> TYPE: DNA
<213> ORGANISM: Artificial Sequence
<220> FEATURE:
<223> OTHER INFORMATION: Synthetic Construct

<400> SEQUENCE: 15
cccgttcccg acctcaccta accggtcgtc ataaccagat gcggggcac ctgcatttat       60 tttatattct gtccg                                                      75
```

ANTI-CYANOBACTERIA RECOMBINANT ANTIBODY POLYPEPTIDE, GENE THEREOF, AND PREPARATION METHOD THEREOF

CROSS-REFERENCE TO RELATED APPLICATIONS

This application is the national phase of PCT application PCT/CN2012/073120 having an international filing date of Mar. 27, 2012, which claims priority to Chinese Patent Application No. 201110100775.2, filed on Apr. 21, 2011 and Chinese Patent Application No. 201110155221.2 filed Jun. 10, 2011. The contents of the above-listed applications are incorporated herein by this reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717412000300SubSeqList.txt, date recorded: Aug. 3, 2015, size: 22,853 bytes).

TECHNICAL FIELD

The present disclosure relates to biotechnology. More specifically, relates to biotechnology in environment protection, especially a recombinant antibody polypeptide, gene thereof, and preparation method thereof.

BACKGROUND

Cyanobacteria proliferation and water pollution caused by water eutrophication are the biggest harm for the worldwide water environment that lead to great economic loss and irreparable damage towards the biosphere of the earth. Along with the accelerated industrialization and urbanization by the economic development of China, environment pollution and degeneration are severer and severer, and bionomic control on water environment has become a crutial problem to be faced and solved.

The present antibacterial agents are hardly effective against cyanobacteria, a prokaryocyte that belongs to Phylum X of cyanobacteria, Domain Bacteria. Currently, there is only heavy metal chemical reagent, for example, copper sulfate and etc, which can control cyanobacteria. However, in practical use against cyanobacteria, the overdosed and repeated use of drugs due to their limited effects destroys against other beneficial algae, aquatic plants, organisms, and brings irreversible and perpetual wreck to the environment, as well as heavy metal agent residue with increasing amount in both the environment and agricultural products. Therefore, it is of great demand for the development of high-effective and safe anti-cyanobacterial drugs.

SUMMARY

In one aspect, the present invention provides genes, recombinant plasmids, and polypeptides of a novel anti-cyanobacteria recombinant antibody polypeptide; said polypeptides are capable of specifically killing cyanobacteria cells but not damaging other algae cells, plants and animals. Another aspect of the present invention is to provide methods for preparing said anti-cyanobacteria recombinant antibody polypeptides.

Provided is a hybridoma with a depository number of CGMCC No. 4783.

Also provided is a monoclonal antibody secreted by said hybridoma.

Also provided is an antibody mimics polypeptide with function of recognizing and binding cyanobacteria, which is an antigen-binding fragment of said monoclonal antibody, or a small molecular polypeptide that is designed on the basis of functional regions of said antigen-binding fragment of said monoclonal antibody.

Said antibody mimic polypeptide, its amino acid sequence sets forth in SEQ ID NO. 3.

Also provided is gene encoding any one of said antibody mimic polypeptides.

Said gene has a nucleotide sequence set forth in SEQ ID NO.2.

Also provided is an anti-cyanobacteria recombinant antibody polypeptide, constructed by operably and linearly connecting said antibody mimic polypeptide capable of recognizing and binding cyanobacteria to the C-terminus of colicin polypeptide, and said colicin is selected from colicin E1, Ia, Ib, A, B or N.

Said anti-cyanobacteria recombinant antibody polypeptide has an amino acid sequence set forth in SEQ ID NO.7.

Also provided is a gene encoding said any one of anti-cyanobacteria recombinant antibody polypeptide.

Said gene has a nucleotide sequence shown in SEQ ID NO.6.

Also provided is a recombinant expression vector, which comprises the gene encoding said anti-cyanobacteria recombinant antibody polypeptide.

Also provided is a method for preparing said anti-cyanobacteria recombinant polypeptide, with steps as follows: transducting the gene encoding the anti-cyanobacteria recombinant antibody polypeptide into an *E. coli* expression system, cultivating the transducted *E. coli*, and separating the polypeptide expressed by *E. coli*.

Also provided is the use of said anti-cyanobacteria recombinant antibody polypeptide on the control of water eutrophication.

The invention provides an anti-cyanobacteria recombinant antibody polypeptide, which is constructed from colicin polypeptide and an antibody mimic polypeptide against cyanobacteria cell surface antigen. In said polypeptide molecule, the antibody mimetics against cyanobacteria cell surface antigen recognizes and binds to cyanobacteria, leading colicin of the molecule to attack the recognized cyanobacteria cell. With an antibody mimetic recognizing cyanobacteria cell surface antigen specifically, the polypeptide of the invention attacks cyanobacteria cells with no damage to other water organisms and no water pollution, thus being environment-protecting and safe on control of water cyanobacteria pollution. The antibody mimetic in the anti-cyanobacteria recombinant antibody polypeptide of the invention is an antibody mimetic capable of recognizing and binding to cyanobacteria, and is designed based on the amino acid sequences and nucleotide sequences of the light and heavy chain of the antigen-binding fragment (Fab) of the monoclonal antibody secreted by hybridoma CGMCC No. 4783, such as mimic antibodies well known in the art, e.g., single-chain antibody and small molecular antibody mimetics, etc. In the invention, the designed antibody mimetic just need to be capable of recognizing the antigen, as the only task of the antibody mimetics is to guide the recombinant polypeptide molecule to target cell surface, and build an ion tunnel on the cell membrane by colicin in the recombinant polypeptide, thereby resulting in the target cell death due to intracellular substance leak. Therefore, any recombinant polypeptides constructed by linking a colicin to an antibody mimetic that is designed on the basis of said monoclonal antibody and can recognize the target antigen, will fall into the claimed scope of the invention.

In an embodiment of the invention, the antibody mimetic is a 28-peptide antibody mimetics constructed by linking domains of $V_H$CDR1, $V_H$FR2 and $V_L$CDR3 of a monoclonal antibody against surface antigen of cyanobacteria protoplast (secreted by hybridoma CGMCC No. 4783) in order of $V_H$CDR1-$V_H$FR2-$V_L$CDR3. Indoor and outdoor experiments proved that, the anti-cyanobacteria polypeptide constructed by said antibody mimetics has biological activity of moving around and automatically looking for the cyanobacteria cell surface antigen in water. The 28-peptide antibody mimetics has advantages that it is easily to be cloned, expressed, and has recognizing activity of the original antibody; it can kill cyanobacteria by guiding the colicin of the recombinant polypeptide to target cell membrane to build an ion tunnel. Said recombinant polypeptide has more ecological and environmental safety, compared with current drugs on controlling water pollution (e.g., copper sulfate).

In the invention, the colicin for the construction of the anti-cyanobacteria recombinant antibody polypeptide may be selected from colicin E1, Ia, Ib, A, B or N that could form ion channel. The recombinant polypeptide constructed by anti-cyanobacteria antibody mimetics and colicin Ia is verified by examples of the invention. However, with the property of forming an ion channel on the cell membrane of cyanobacteria, any of these colicins according to conception of the invention may be linked linearly to anti-cyanobacteria antibody mimetics for constructing the recombinant polypeptide to carry out the invention, that is, to provide recombinant polypeptides that kill cyanobacteria.

The invention also provides preparation method of the recombinant plasmid comprising the gene of recombinant polypeptide, wherein the nucleotide sequence encoding antibody mimetics is inserted into the C-terminus of colicin by double strand oligonucleotides site-directed mutagenesis, to form the recombinant plasmid of the invention. Taking colicin Ia as an example, the recombinant plasmid of the invention is constructed by inserting the nucleotide sequence encoding antibody mimetics into the site after amino acid 626 of colicin Ia gene (the C-terminus). The original vector pSELECT-1 is purchased from Promega Corp., which contains genes of colicin Ia and Immunity protein. In Example 1 of the present invention, several pairs of primer sequences are designed for genes of antibody mimetics. The recombinant plasmid, e.g. pCHCcyanoMA1, is prepared according to the instruction of the kit from Strategene Corp. by double strand oligonucleotides site directed mutagenesis.

In another aspect of the invention, provided is a preparation method of said anti-cyanobacteria polypeptide of the invention, wherein a recombinant plasmid comprising a gene encoding anti-cyanobacteria recombinant antibody polypeptide is obtained by operably linking a gene encoding antibody mimetics with a colicin gene, and the obtained recombinant plasmid is transfected into an *E. coli* engineering bacteria to obtain a engineering bacteria cell that may produce anti-cyanobacteria recombinant antibody polypeptide. Said anti-cyanobacteria polypeptide of the invention is then obtained from separation and purification with ion-exchange column.

Said anti-cyanobacteria polypeptide of the invention may be used in the control of water pollution. Drug combinations suitable for environment may be prepared by adding vectors, excipients, or other alternative components into the polypeptide of the invention, wherein the mechanism is as follows: antibody mimetics within the polypeptide that recognize cyanobacteria cell surface antigen guide colicin to the cyanobacteria cell membrane with the hydrophobic fragment of ion channel domain in colicin inserted into, to form an ion channel, thereby cyanobacteria cell death is incurred by intracellular substance leak.

Said anti-cyanobacteria polypeptide of the invention has an advantage of target specificity compared with traditional anti-cyanobacterial drugs, thus it does not attack other algae, plants and animal cells; toxicity and untoward effect far less than traditional anti-cyanobacterial drugs. Furthermore, since the ion channel is directly formed on cyanobacteria cell membrane to kill cyanobacteria cells, it is difficult for cyanobacteria cells to repair the geometrical damages on cell membrane by way of gene mutation and protein expression, in the short time of intracellular substance leak through anti-cyanobacteria polypeptide ion channel to cyanobacteria cell death. Therefore, it is with low probability that cyanobacteria cells obtains drug resistance of the anti-cyanobacteria polypeptide of the invention, which indicates there is a promising application prospect to said anti-cyanobacteria polypeptide of the invention.

Deposit Information of Hybridoma:

Deposit Number: CGMCC No. 4783

Deposit Name: Monoclonal antibody hybridoma against cyanobacteria cell surface antigen Depository Date: Apr. 20, 2011

Depositary institution: China General Microbiological Culture Collection Center, CGMCC Address: No. 3, Courtyard No. 1, Beichen West Road, Chaoyang District, Beijing

DESCRIPTION OF DRAWINGS

FIG. 1 schematic illustration of the structure of recombinant plasmid pCHCcyanoMA1 comprising genes of antibody mimetics and colicin Ia FIG. 2 schematic illustrates the structure of the anti-cyanobacteria recombinant antibody of present invention.

FIG. 3 schematic illustration of the structure of recombinant plasmid pCHCcyanoMA2 comprising genes of antibody mimetics and colicin Ia with reversed N-C order in part.

FIG. 4 the experiment results about the inhibition of the anti-cyanobacteria polypeptide of the invention on *Microcystis aeruginosa* cultivated in liquid medium, Wherein, A, blank control; B, 50 μg/ml of ampicillin; C, broad 50 μg/ml of spectrum pheromone (Ph-NM); D, 50 μg/ml of anti-cyanobacteria polypeptide (1); E, 50 μg/ml of anti-cyanobacteria polypeptide (2).

FIG. 5 the experiment results about the inhibition of the anti-cyanobacteria polypeptide (1) of the invention on *Microcystis aeruginosa* cultivated in liquid medium Wherein, A, result of treating for 48 hours; B, result of treating for 72 hours; C, result of treating for 96 hours.

Wherein, there are 6 flasks in each column, from left to right, namely as follows: 1, control; 2, 0.1 μg/ml of anti-cyanobacteria polypeptide (1); 3, 0.5 μg/ml of anti-cyanobacteria polypeptide (1); 4, 1 μg/ml of anti-cyanobacteria polypeptide (1); 5, 5 μg/ml of anti-cyanobacteria polypeptide (1); 6, 10 μg/ml of anti-cyanobacteria polypeptide (1).

FIG. 6 the experiment results about the inhibition of the anti-cyanobacteria polypeptide (1) of the invention on *Scenedesmus* cultivated in liquid medium.

Wherein, there are 6 flasks in each column which are treated for 10 days, from left to right, namely as follows: 1, control; 2, 1 μg/ml of anti-cyanobacteria polypeptide (1); 3, 5 μg/ml of anti-cyanobacteria polypeptide (1); 4, 10 μg/ml of anti-cyanobacteria polypeptide (1); 5, 15 μg/ml of anti-cyanobacteria polypeptide (1); 6, 20 μg/ml of anti-cyanobacteria polypeptide (1).

Figure 7:
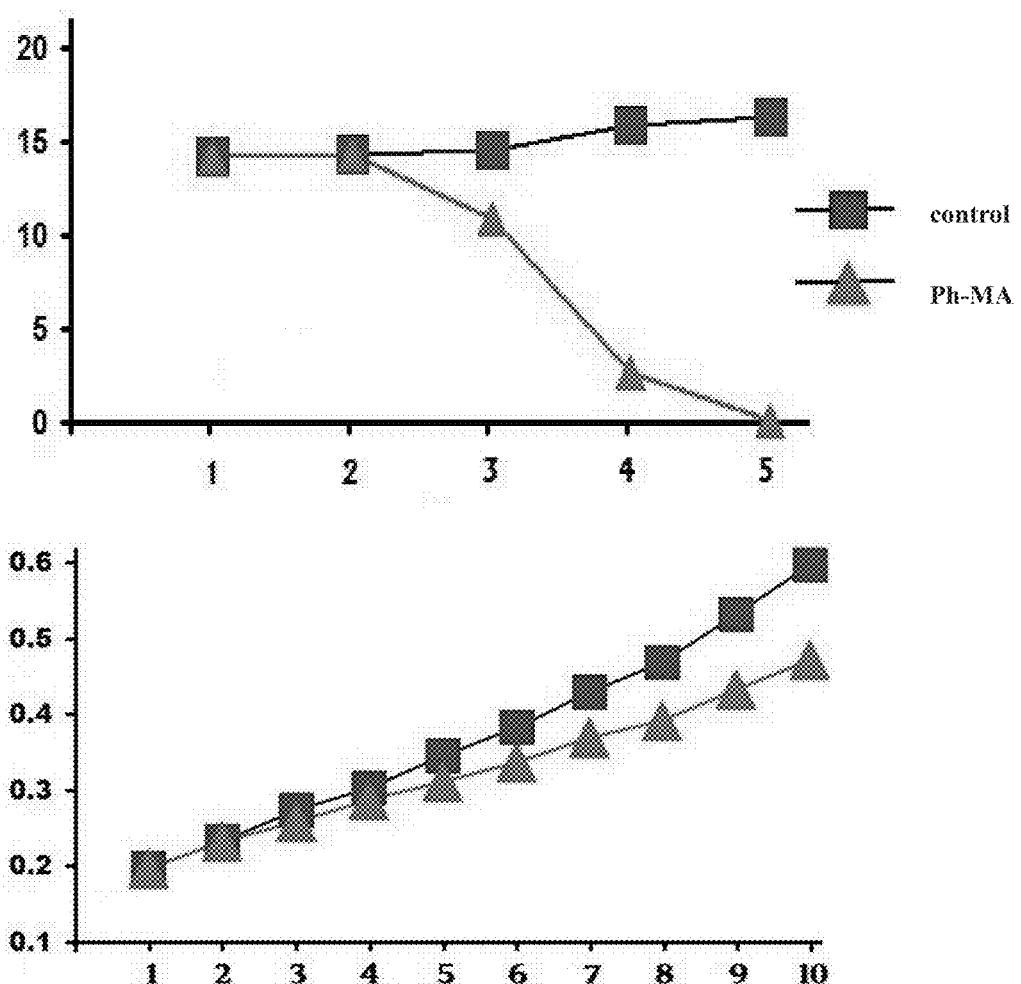
Figure 8A:
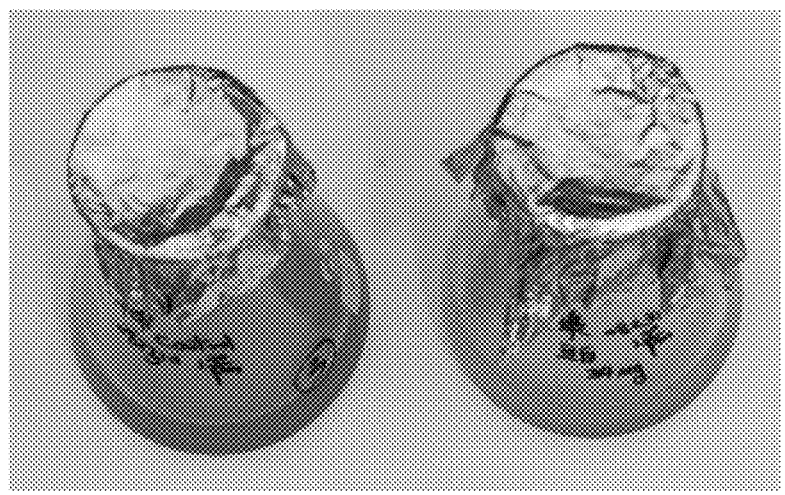
Figure 8B:
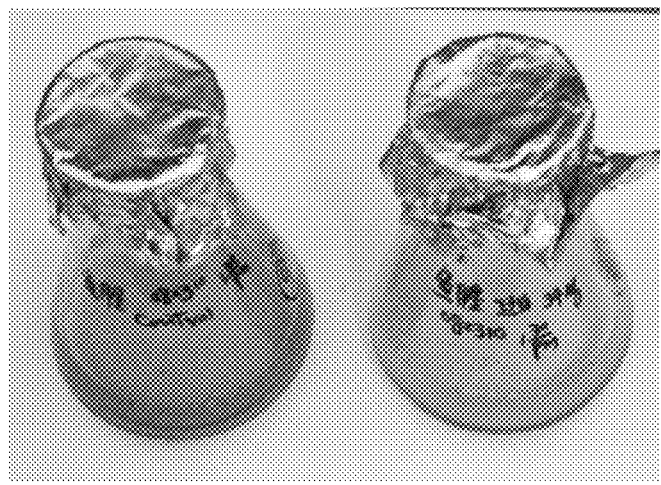
Figure 8C:
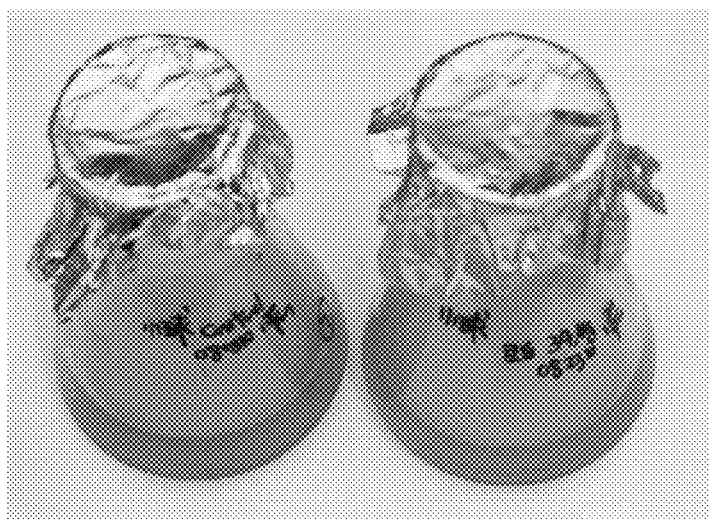
Figure 8D:
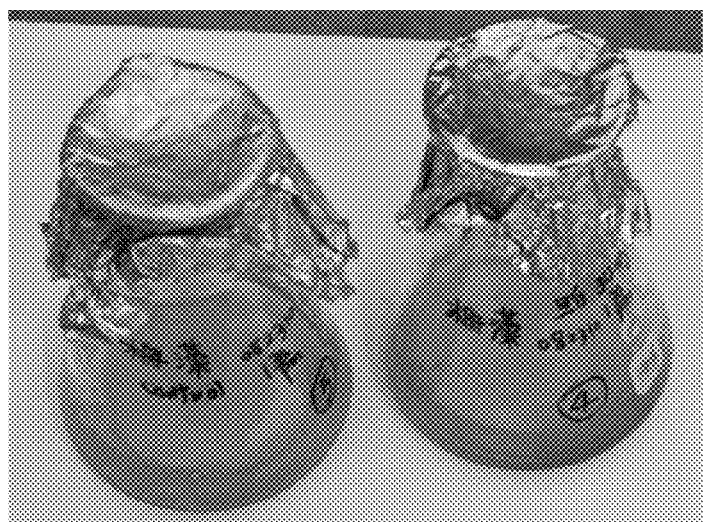

FIG. 7 the experiment results about the inhibition of the anti-cyanobacteria polypeptide (1) Ph-MA of the invention on *Microcystis aeruginosa* and *Scenedesmus* cultivated in liquid medium.

Wherein, the result of *Microcystis aeruginosa* is shown in the upper part, and that of *Scenedesmus* is shown in the lower part.

FIG. 8 the experiment results about the inhibition of the anti-cyanobacteria polypeptide of the invention on *Microcystis aeruginosa, Anabaena, Chlorella,* and *Scenedesmus* cultivated in liquid medium.

Wherein, the left flask is control, and the right one is 35 μg/ml of anti-cyanobacteria polypeptide (1). Wherein A: *Microcystis aeruginosa*; B: *Anabaena*; C: *Chlorella*; D: *Scenedesmus*.

Figure 9:
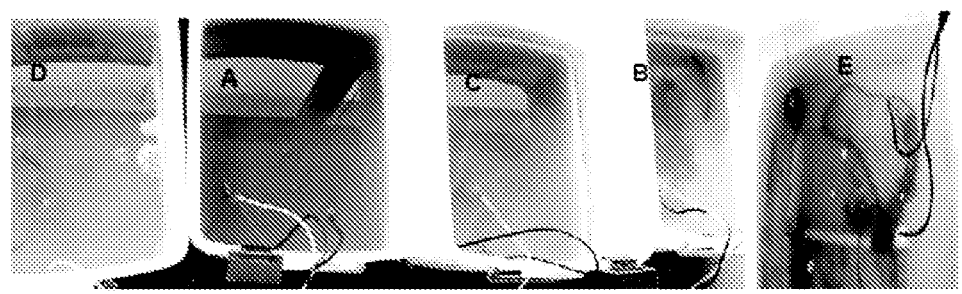
Figure 10A:
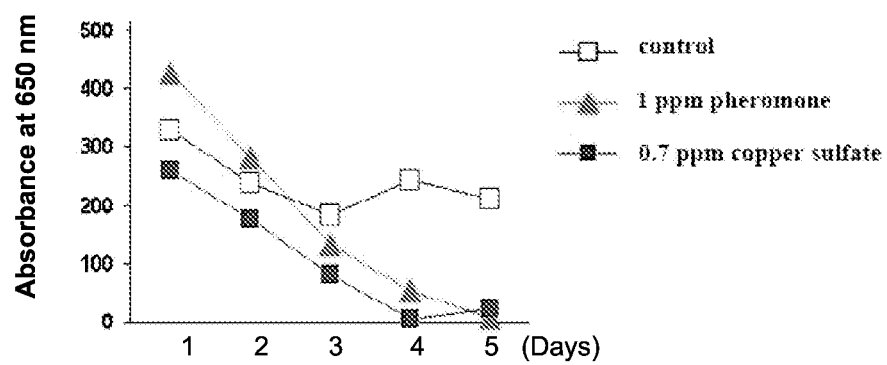
Figure 10B:
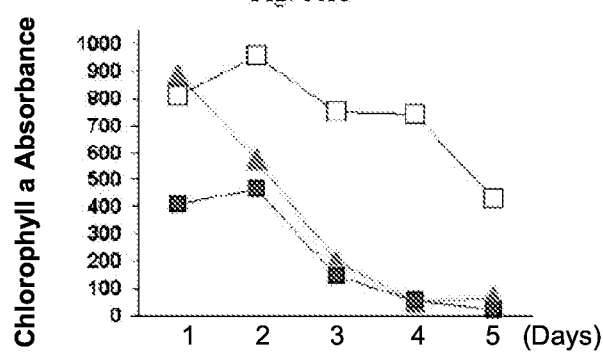
Figure 10C:
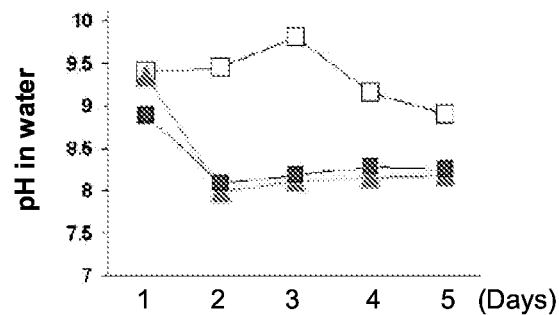
Figures 1, 10D:
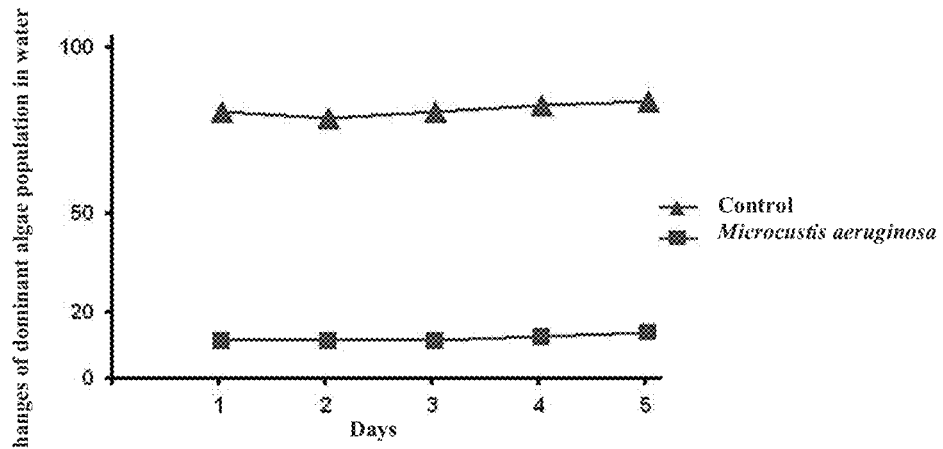
Figures 2, 10D:
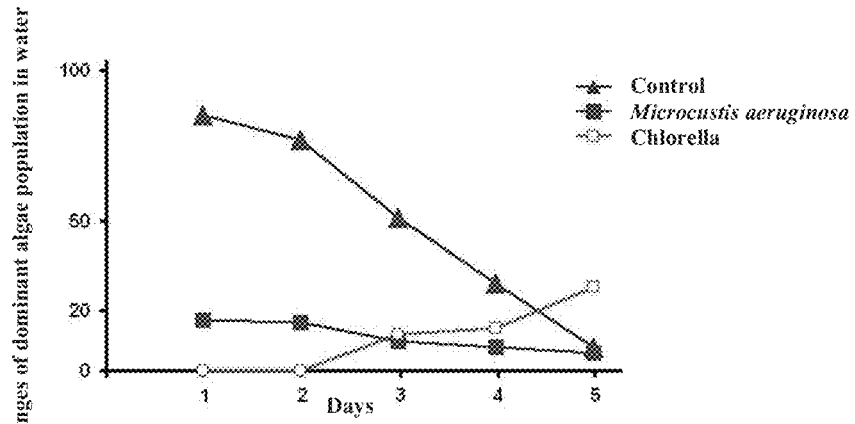
Figures 3, 10D:
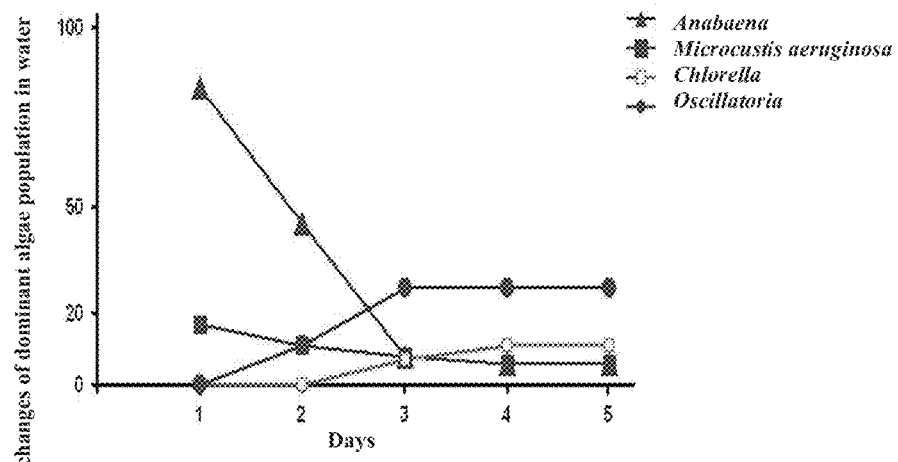
Figure 11A:
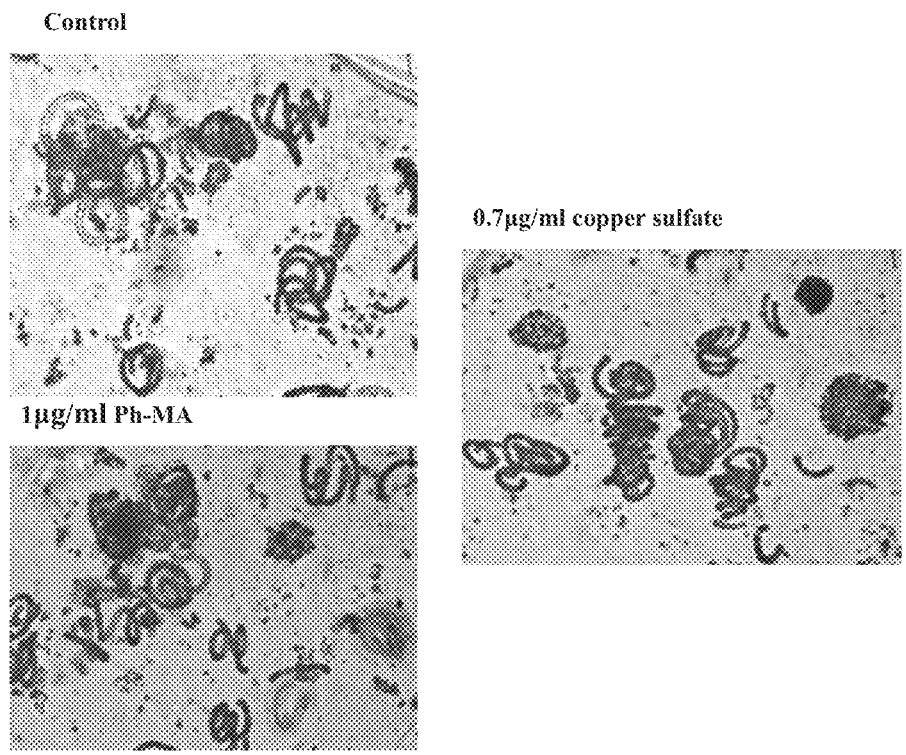
Figure 11B:
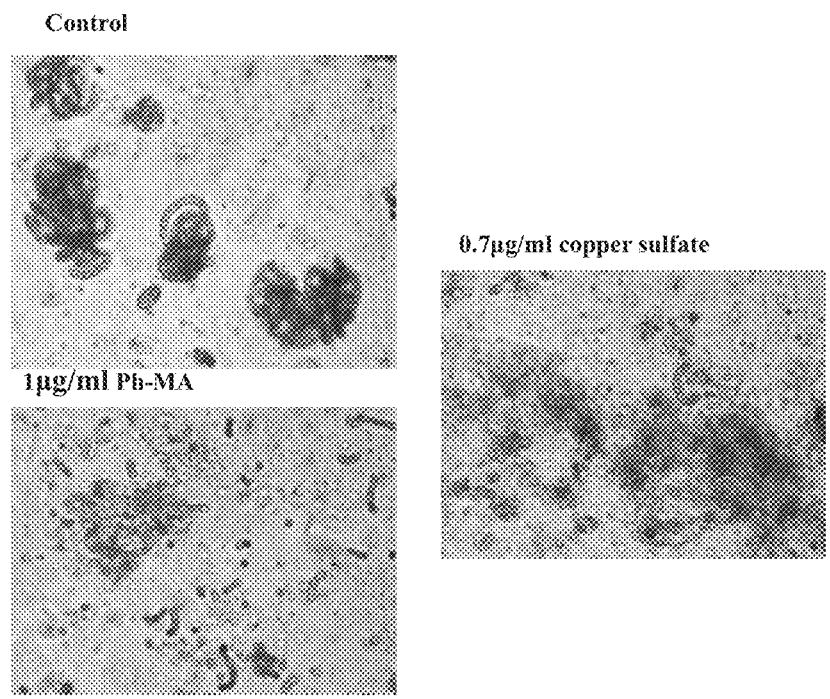
Figure 11C:
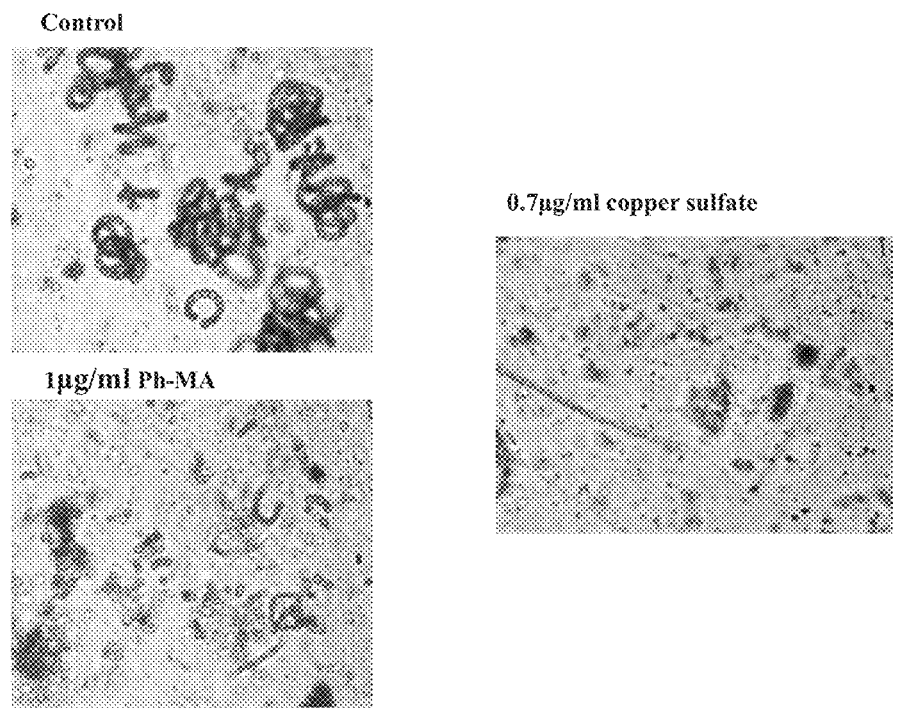
Figure 11D:
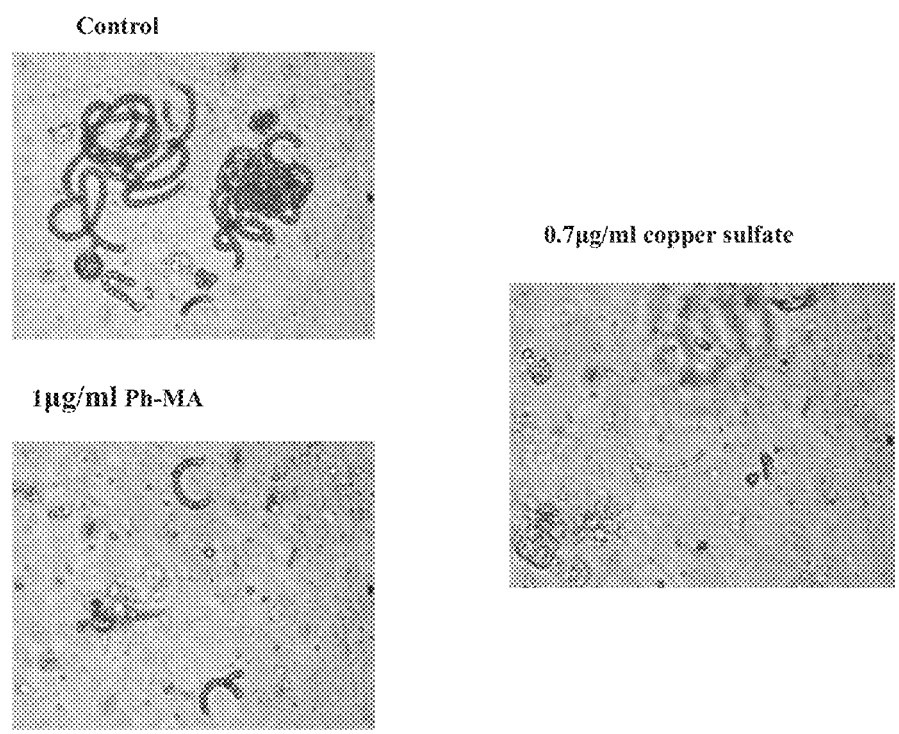
Figure 11E:
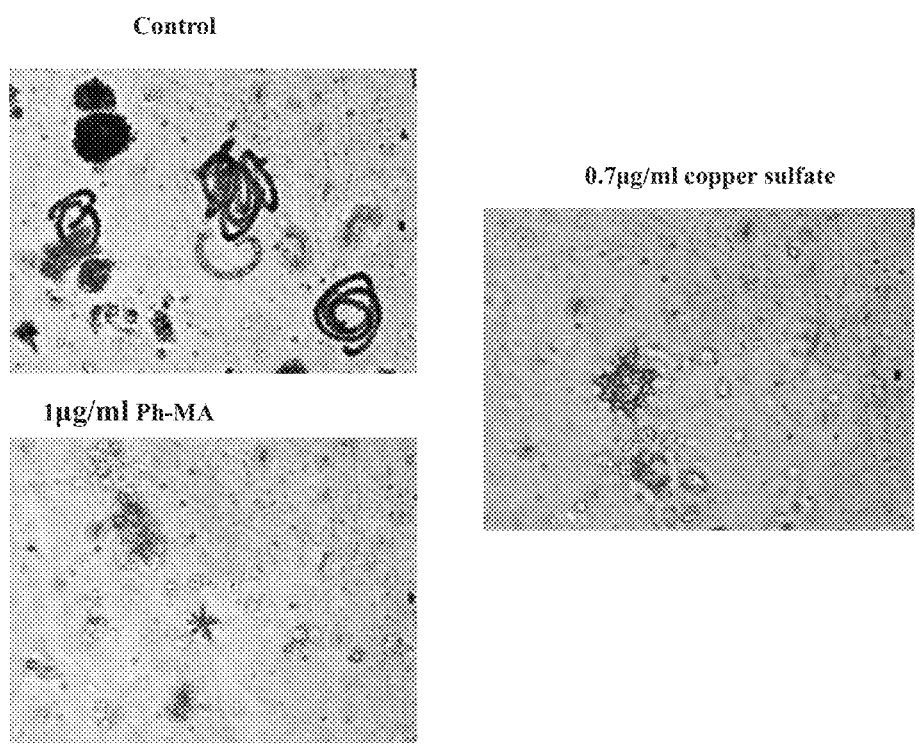

FIG. 9 the experiment result about the inhibition of the anti-cyanobacteria polypeptide of the invention on the natural water polluted by cyanobacteria.

Wherein, A, blank control; B, 1 μg/ml of anti-cyanobacteria polypeptide (1); C, 5 μg/ml of anti-cyanobacteria polypeptide (1); D, 10 μg/ml of anti-cyanobacteria polypeptide (1); E, 0.7 μg/ml of copper sulfate.

FIG. 10 some respects of results of the inhibition experiment in FIG. 9

Wherein, A, changes of optical density in water; B, changes of Chlorophyll a in water; C, pH changes in water; D, changes of dominant algae population in water.

Wherein, D-1, Control group; D-2, the group treated by 1 μg/ml of anti-cyanobacteria polypeptide (1); D-3, the group treated by 0.7 μg/ml of copper sulfate.

FIG. 11 microscopic observation (magnified by 400-fold) of the inhibition of the anti-cyanobacteria polypeptide Ph-MA on natural water polluted by cyanobacteria in FIG. 9

Wherein, changes of algae (*Anabaena*) that is treated by control, 1 μg/ml of anti-cyanobacteria polypeptide (1) and 0.7 μg/ml of copper sulfate in water on the first Day 1 (A), the second Day (B), the third Day (C), the fourth Day (D), the fifth Day (E) are shown respectively.

DETAILED DESCRIPTION

Example 1

Construction of Plasmid Expressing Anti-Cyanobacteria Polypeptide and Preparation of Anti-Cyanobacteria Recombinant Polypeptide Material: Hybridoma CGMCC No. 4783.

Step 1. Obtaining of the nucleotide sequence and amino acid sequence of antibody mimetics: the monoclonal antibody secreted by hybridoma was collected and sequenced by using conventional methods to obtain the sequence of heavy chain and light chain of antigen-binding fragment Fab; the amino acid sequence of antibody mimetics was designed on the basis of the amino acid sequence of complementarity-determining regions, as shown in SEQ ID NO.3. The nucleotide sequence encoding said antibody mimetics is set forth in SEQ ID NO.2.

Step 2. The original vector is the plasmid pSELECT-1 (purchased from Promega Corp.), which carries genes of colicin Ia and Immunity protein (said genes are loaded in the lab where the experiments of this invention are conducted). The gene encoding anti-cyanobacteria antibody mimetics (nucleotide sequence shown in SEQ ID NO.2 in the sequences listing) was inserted after the site of 1626 on the gene of colicin Ia by double-strand oligonucleotide Site-Directed Mutagenesis technology (QuickChange™ Kit, Strategene Corp.), to obtain a recombinant plasmid pCHCcyanoMA1 (as shown in FIG. 1). The recombination plasmid was then transfected into the engineering bacteria of *E. coli* B834 (DE3) to prepare the polypeptide. Said anti-cyanobacteria polypeptide with amoni acid sequence shown in SEQ ID NO.7 (hereinafter referred to as "anti-cyanobacteria polypeptide (1)") and molecular weight about 70,000 was obtained.

The process of double-strand oligonucleotide site-directed mutagenesis was performed according to the manual of Strategene QuickChange Site-Directed Mutagenesis Kit (catalog #200518).

1. Preparation of reactants for site-directed mutagenesis:
   5 μl 10× buffer
   2 μl (10 ng) wild-type colicin Ia plasmid
   1 μl (125 ng) 5'-3' oligonucleotide primers as designed
   1 μl (125 ng) 5'-3' oligonucleotide primers as designed
   1 μl dNTP
   Double-distilled water 50 μl
   1 μl pfu
   (All is provided in the Kit except for the plasmid, primers and double-distilled water)

Figure 2:
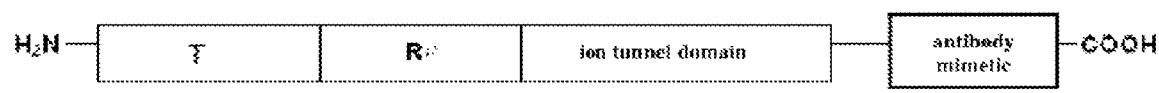
Figure 3:
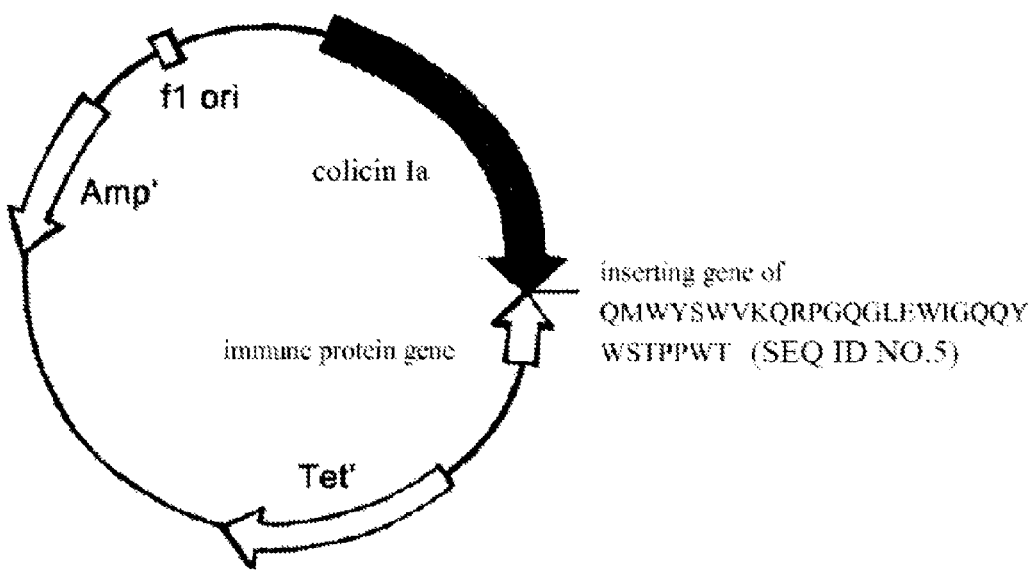
Figure 4A:
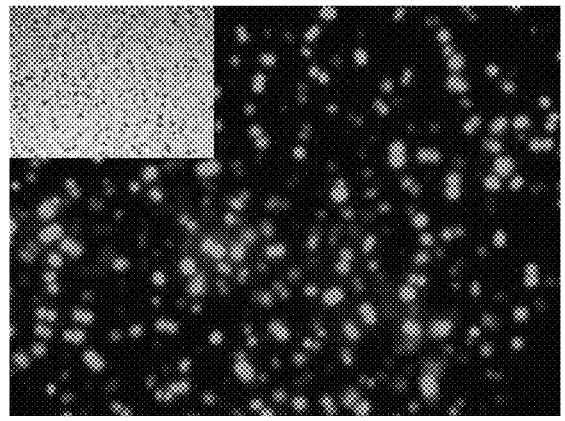
Figure 4B:
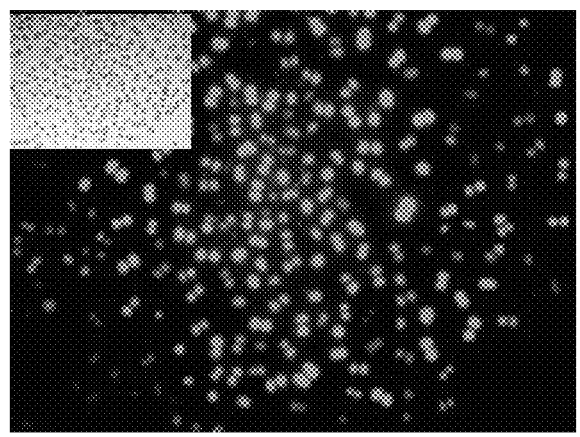
Figure 4C:
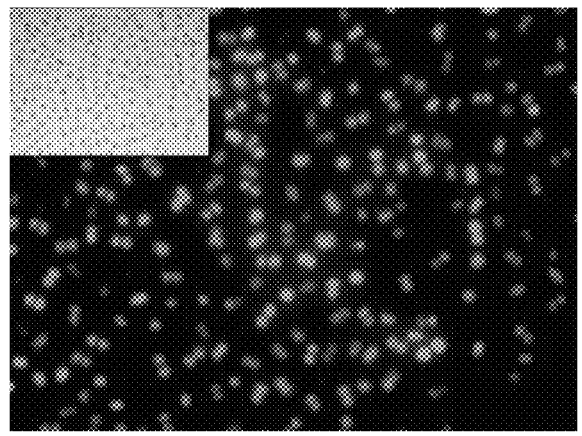
Figure 4D:
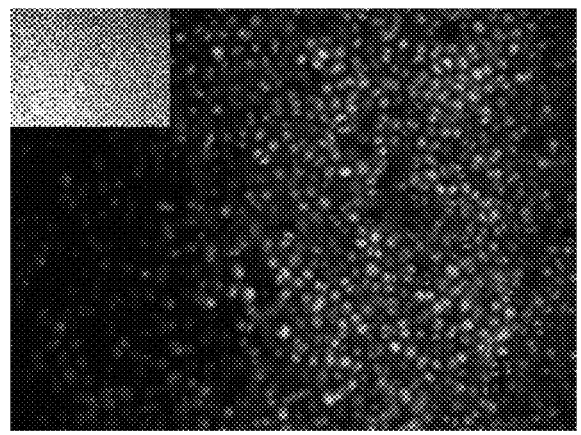
Figure 4E:
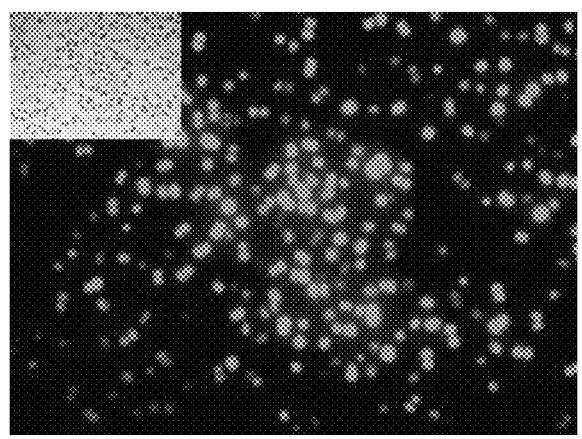

2. PCR amplification, amplification conditions: 20 cycles of denaturation at 95° C. for 35 seconds, anneal at 53° C. for 70 seconds, and extension at 68° C. for 17 minutes;

3. 1 μl of endonuclease Dpn 1 was added to digest DNA chain (37° C., 1 hour); 1 μl of reactant and 50 μl of HMS174 competent cell were incubated together in ice for 30 minute, and then incubated in ice for 2 minute after a heat shock at 42° C. for 45 seconds;

4. 0.5 ml of culture medium NZY was added, and cultivated by shaking at 37° C., 220 rpm for 1 hour. 50-100 μl of reactant was spread on LB medium plate plus 1% agar and 50 μg/ml of ampicillin for cultivating overnight at 37° C.;

5. Colonies were picked up after cultivating for 18 hours. Plasmid was extracted by using extraction Kit of Qiagene Corp. or Gibco Corp., and then sequenced to confirm if the mutation is successful;

6. 50 ng of recombination plasmid was incubated with 50 μl of the prepared *E. coli* B834 (DE3) competent cells in ice for 30 minute, and heat shocked at 42° C. for 30 second. 50-100 μl of the reactant was added with 0.5 ml of SOC culture medium, cultivated by shaking at 37° C., 220 rpm for 1 hour and spread on LB medium plate plus 1% agar and 50 μg/ml of ampicillin for incubating at 37° C. for 12-16 hours. Afterwards, single colony was picked up;

7. Bacteria were amplified in 8-16 liters of LB medium at 250 rpm, 37° C. for 6-8 hours. The bacterium was precipitated by centrifugation at 6000 g, 4° C. for 20 minutes, resuspended with 50-80 ml of 50 mM Borate, 2 mM EDTA (pH 9.0) at 4° C.; 250 microliters of 0.2M PMSF was added and treated with ultrasonication at 4° C., 400 W for 2 minutes. Bacterium debris was high-speed centrifugated at 4° C., 75,000 g for 1.5 hours. The supernatant was added with streptomycin sulphate to precipitate DNA, dialyzed overnight in dialysis bag with molecular weight of 15,000 as well as with 10 L of 50 mM Borate, 2 mM EDTA, pH 9.0 buffer at 4° C., and then loaded on a CM column (Amersham Biosciences). The column was eluted by a buffer of 50 mM Borate, 0.3 M NaCl, 2 mM EDTA, pH 9.0 to obtain the anti-cyanobacteria recombinant polypeptide (1) (See FIG. 2)

Sequences of double strand oligonucleotides designed for the preparation on genes of antibody mimetics of the plasmid pCHCcyanoMA1 are as follows:

pCHCcyanoMA1
1. 5'-3'
(SEQ ID NO. 10)

gcg aat aag ttc tgg ggt att TCT TAT TGG ATG CAG TGG GTT AAG CAA taa ata aaa tat aag aca ggc

3'-5'
(SEQ ID NO. 11)

gcc tgt ctt ata ttt tat tta TTG CTT AAC CCA CTG CAT CCA ATA AGA aat acc cca gaa ctt att cgc 2. 5'-3'
(SEQ ID NO. 12)

tat tgg atg cag tgg gtt aag caa AGA CCG GGG CAA GGG CTG GAG TGG ATT

GGC taa ata aaa tat aag aca ggc

3'-5'
(SEQ ID NO. 13)

gcc tgt ctt ata ttt tat tta GCC AAT CCA CTC CAG CCC TTG CCC CGG TCT ttg ctt aac cca ctg cat cca ata 3. 5'-3'
(SEQ ID NO. 14)

ggg caa ggg ctg gag tgg att ggc CAG CAG TAT YGG TCT ACG CCC CCG TGG

ACG taa ata aaa tat aag aca ggc

3'-5'
(SEQ ID NO. 15)

gcc tgt ctt ata ttt tat tta CGT CCA CGG GGG CGT AGA CCA ATA CTG CTG gcc aat cca ctc cag ccc ttg ccc

Example 2

Figure 5:
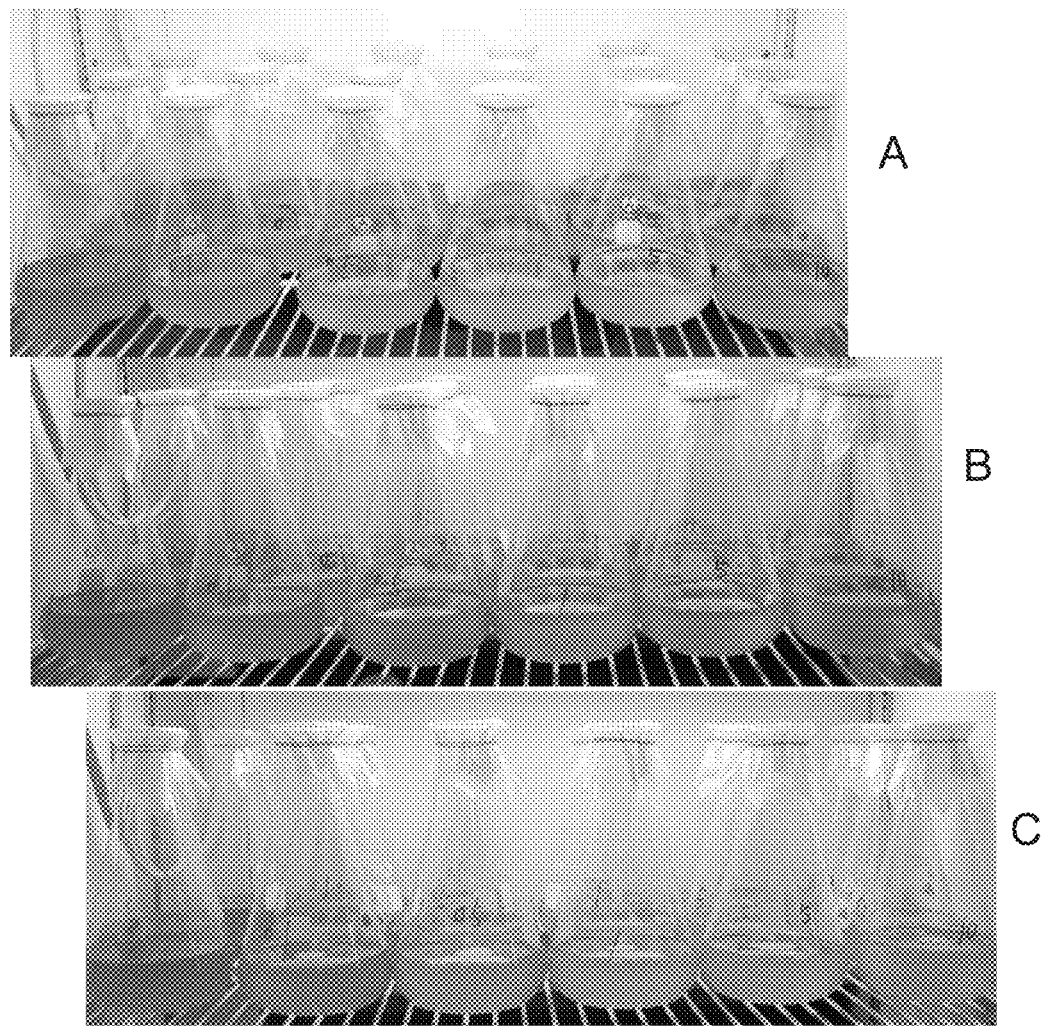

Construction of a Control Plasmid Expressing Anti-Cyanobacteria Polypeptide and Preparation of the Control Anti-Cyanobacteria Polypeptide The original vector is the plasmid pSELECT-1 (purchased from Promega Corp.), which carries genes of colicin Ia, and Immunity protein (said genes are loaded in the lab where the experiments of this invention are conducted). The gene encoding anti-cyanobacteria antibody mimetics (nucleotide sequence shown in SEQ ID NO.4 in the sequence list) was inserted after the site of 1626 on the gene of colicin Ia by double-strand oligonucleotide Site-Directed Mutagenesis technology (QuickChange™ Kit, Strategene Corp.) to obtain recombinant plasmid pCHCcyanoMA2 (as shown in FIG. 3). The recombination plasmid was transfected into the engineering bacteria of *E. coli* B834 (DE3) to prepare the polypeptide. Said anti-cyanobacteria polypeptide whose sequence list is shown in SEQ ID NO.9 (hereinafter referred to as "anti-cyanobacteria polypeptide (2)") and the molecular weight is about 70,000 was obtained.

Sequences of double strand oligonucleotides for the preparation on genes of antibody mimetics of the plasmid pCHCcyanoMA2 was designed and prepared according to the method in Example 1.

Example 3

Experiment Results of Inhibition of Anti-Cyanobacteria Polypeptide on *Microcystis aeruginosa*

Experiment (1)

Step 1. Preparation of algae for experiment: *Microcystis aeruginosa* FACHB-978 is purchased from the Institute of Hydrobiology, Chinese Academy of Sciences.

Cultivation method of the algae: algae seed was inoculated with an initial cell density of $5\times10^4$/mL into a 500 ml conical flask containing 250 ml of BG11 medium and placed into an illumination incubator, wherein the conical flask was covered with breathable film to prevent pollutions. Algae were cultivated at 25° C. with illumination intensity of (2500±10%) lux and light/dark ratio of 12 h/12 h. Conical flasks were shaked and position-exchanged once every 2-3 hours. Samples were taken and tested once every 24 hours since the 5th day after the inoculation. The next step could be performed till the cell density reached about $10^6$/mL.

Step 2. 1 ml of prepared cyanobacteria liquid is added respectively into 5 tubes, namely, A, B, C, D, and E, and then inhibitors were added as follows: A, blank control; B, 50 μg/ml of ampicillin; C, 50 μg/ml of broad spectrum pheromone (Ph-AM1 disclosed in Patent Application No. CN200910092128.4); D, 50 μg/ml of anti-cyanobacteria polypeptide (1); E, 50 μg/ml of anti-cyanobacteria polypeptide(2). After shaking cultivation at low speed for 12 hours in a incubator, the 5 tubes were respectively added with acridine orange (50 nM) and propidium iodide (600 nM) for incubating for 30 min; several microliters were sampled onto a slide to observe the alive stained cyanobacteria by a fluorescence microscope (Nikon 90i with filter of DM505 and DM565).

Results are shown in FIG. 4. It's manifested by results that only anti-cyanobacteria polypeptide (1) killed the cultivated *Microcystis aeruginosa*, whereas none of anti-cyanobacteria polypeptide (2), ampicillin and Ph-NM showed effects on the cultivated *Microcystis aeruginosa.*

Experiment (2)

Step 1. It was same as in Step 1 in Experiment (1).

Step 2. Anti-cyanobacteria polypeptides were added by concentration gradient into 6 of 500 ml conical flasks filled with algae. The anti-cyanobacteria polypeptide was added to *Microcystis aeruginosa* in doses of 0, 0.1, 0.5, 1, 5, and 10 μg/ml. The inhibition on cyanobacteria was observed every day.

Results were shown in FIG. 5. Because the concentration of anti-cyanobacteria polypeptide (1) was different in each group, the time of colour changing from green to light yellow of *Microcystis aeruginosa* liquid in each conical flask was proportional to the concentration of anti-cyanobacteria polypeptide (1). However, it was observed visually that *Microcystis aeruginosa* in all treatment could be killed effectively in 72 hours.

The above result showed that anti-cyanobacteria polypeptide (1) is capable of target killing the cultivated *Microcystis aeruginosa*, whereas anti-cyanobacteria polypeptide (2) hardly shows any effect.

Experiment (3)

Material: *Scenedesmus obliqnus* FACHB-417 is purchased from the Institute of Hydrobiology, Chinese Academy of Sciences, and cultivated according to the method in Step 1 of Experiment (1).

Step 2. Anti-cyanobacteria polypeptide (1) was added into 6 of 500 ml conical flasks with algae by concentration gradient 0, 1, 5, 10, 15, and 20 μg/ml respectively. The inhibition on *Scenedesmus* was observed every day.

Figure 6:
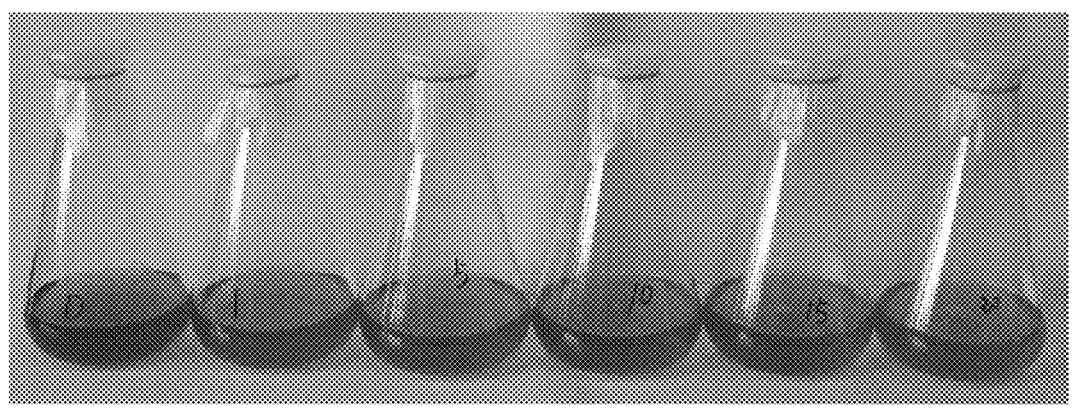

Results are shown in FIG. 6. Although the dose of anti-cyanobacteria polypeptide (1) was 10 times higher than that added in *Microcystis aeruginosa*, no killing effect of anti-cyanobacteria polypeptide (1) on *Scenedesmus* was observed visually during the experiment (190 hours).

Experiment (4)

0.1 mL of culture liquid is taken from each flask of the Experiment (1)-(3) and placed in a blood counting chamber for observing and counting under a microscope. It's shown by the algae cell number in FIG. 7 that, compared to the control, 1 μg/ml of anti-cyanobacteria polypeptide (1) can kill *Microcystis aeruginosa* in 72 hours, whereas 1 μg/ml of anti-cyanobacteria polypeptide (1) hardly showed any effect against *Scenedesmus*.

Example 4

Experiment of Anti-Cyanobacteria Polypeptide Against *Microcystis aeruginosa, Anabaena, Chlorella* and *Scenedesmus* in Liquid Culture Medium

*Microcystis aeruginosa, Anabaena, Chlorella* and *Scenedesmus* are purchased from the Institute of Hydrobiology, Chinese Academy of Sciences, cultivated and treated according to the methods in Step 1, Experiment (1) of Example 3.

40 ml of the algae liquid with cell density of $10^6$/mL was distributed into two 300 ml conical flasks, and added respectively with A: blank control liquid with same amount, B: 35 μg/ml of anti-cyanobacteria polypeptide (1), and cultivated for 4 days. The growth was observed.

Results were shown in FIG. 8. After 24 hours, the color of algae liquid of *Microcystis aeruginosa* and *Anabaena* turned light and became clear on the fourth Day, whereas the colour and turbidity of *Chlorella* and *Scenedesmus* liquid stayed constant. It's illustrated by the results that, anti-cyanobacteria polypeptide 1 inhibited the growth of the *Microcystis aeruginosa* and *Anabaena*, but did not inhibit the growth of *Chlorella* and *Scenedesmus*.

The above results proved that anti-cyanobacteria polypeptide (1) is capable of target killing cyanobacteria.

Example 5

Experiment of Killing Cyanobacteria in Natural Water by Anti-Cyanobacteria Polypeptide Natural water seriously polluted by cyanobacteria was taken from a shrimp breeding pool of Suzhou Yangcheng Lake, 25~35 L of the water was distributed into plastic breeding basins of 60×40×30 cm, with 10 min of air supply by bumping in every 20 min, temperature automatically adjusted to 27° C., illumination intensity of (2500±10%) lux and light/dark ratio of 12 h/12 h. Water was sampled every day to detect the pH, absorbance at 650 nm, and Chlorophyll a absorbance (See FIG. 9).

The absorbance at 650 nm was detected by placing the sample liquid into a visible spectrophotometer (See FIG. 10).

Chlorophyll a content was detected by using hot ethanol-freeze thawing-spectrophotometry method (See FIG. 10). The absorbances at 650 and 700 nm were detected by a spectrophotometer to calculate concentration of Chlorophyll a, with a formula of:

$$[Chla]=[12.12(D664-D750)-1.58(D647-D750)-0.08(D630-D750)]VE/VS\cdot d.$$

PH, absorbance at 650 nm, and Chlorophyll a absorbance in water of the control group remained high during the experiment, whereas those of the anti-cyanobacteria polypeptide (1) group and copper sulfate group decreased dramatically since the second day.

30 ml of water was sampled every day, fixed with formalin, and then concentrated for 10 times by centrifugation. 0.1 mL was taken into a blood counting chamber to be observed and counted under a microscope (See FIG. 11). It's displayed by microscopic examination that, on the first day, plenty of blossoming *Anabaena* could be seen in control group, anti-cyanobacteria polypeptide (1) group and copper sulfate group; whereas since the second day, *Anabaena* in anti-cyanobacteria polypeptide (1) group and copper sulfate group decreased and fragmented greatly in water; and no *Anabaena* could be seen in anti-cyanobacteria polypeptide (1) group and copper sulfate group on the fifth day, but plenty of *Anabaena* in control group were still alive.

Changes of algae shape was observed under a microscope, and various algae were counted to detect the dynamic changes about dominant population of floating plants in water (See FIG. 10). In control group, *Anabaena* and *Microcystis aeruginosa* were dominant algae all the time; in anti-cyanobacteria polypeptide (1) group, *Anabaena* and *Microcystis aeruginosa* decreased gradually while *Chlorella* became dominant; in copper sulfate group, *Anabaena* and *Microcystis aeruginosa* decreased gradually, and another *Cyanobacteria*, the *Oscillatoria*, became dominant.

TABLE 1

Number count and shape change of floating plants treated by anti-cyanobacteria polypeptide (/L)

| | 1st Day of treating | 2nd Day | 3rd Day | 4th Day | 5th Day |
|---|---|---|---|---|---|
| Control group | 32745 | 26363 | 33194 | 41068 | 17954 |
| | | No change in algae shape | No change in algae shape | No change in algae shape | No change in algae shape |

TABLE 1-continued

Number count and shape change of floating plants treated by anti-cyanobacteria polypeptide (/L)

| | 1st Day of treating | 2nd Day | 3rd Day | 4th Day | 5th Day |
|---|---|---|---|---|---|
| 1 mg/L of polypeptide | 50394 | 43981 Most Anabaena became single cells or short chains of 2-5 cells | 10624 Most of Anabaena become short chains of 1-5 cells, without long chain | 5370 Most of Anabaena become short chains of 1-5 cells with little amount | 3432 Almost no Anabaena cells |
| 5 mg/L of polypeptide | 43987 | 40828 Same as the change treated by 1 mg/L polypeptide | 20744 Same as the change treated by 1 mg/L polypeptide | 9890 Same as the change treated by 1 mg/L polypeptide | 3680 Almost no Anabaena cells |
| 10 mg/L of polypeptide | 48101 | 41787 Same as the change treated by 1 mg/L polypeptide | 23443 Same as the change treated by 1 mg/L polypeptide | 14214 Same as the change treated by 1 mg/L polypeptide | 4902 Almost no Anabaena cells |
| 20 mg/L of polypeptide | 45588 | 39194 Same as the change treated by 1 mg/L polypeptide | 33453 Same as the change treated by 1 mg/L polypeptide | 4800 Almost no Anabaena cells | 3508 Almost no Anabaena cells |
| 0.7 mg/L of copper sulfate | 22930 | 1266 all Anabaena became single cells | 499 Almost all the algae became organic detritus | 305 Few algae | 379 Few algae |

Results are shown in FIGS. 9-11 and Table 1. It's manifested by results that 0.7 ppm copper sulfate killed all kinds of algae without selection. However, anti-cyanobacteria polypeptide (1) has targeting inhibition on the growth of cyanobacteria (*Anabaena*, *Microcystis aeruginosa*) in water, but has little influence on the growth of other phytoplankton.

The invention claimed is:

1. An antibody mimetic polypeptide capable of binding to cyanobacteria, said antibody mimetic polypeptide comprising the amino acid sequence set forth in SEQ ID NO. 3.

2. A polynucleotide encoding the antibody mimetic polypeptide of claim 1.

3. The polynucleotide according to claim 2, said polynucleotide comprising the nucleotide sequence set forth in SEQ ID NO. 2.

4. An anti-cyanobacteria recombinant antibody polypeptide, comprising a colicin polypeptide and the amino acid sequence set forth in SEQ ID NO. 3 said amino acid sequence operably and linearly linked to the C-terminus of the colicin polypeptide, wherein said colicin is selected from the group consisting of colicin E1, Ia, Ib, A, B, and N.

5. The anti-cyanobacteria recombinant antibody polypeptide according to claim 4, comprising the amino acid sequence set forth in SEQ ID NO. 7.

6. A polynucleotide encoding the anti-cyanobacteria recombinant antibody polypeptide of claim 4.

7. The polynucleotide according to claim 6, said polynucleotide comprising the nucleotide sequence set forth in SEQ ID NO. 6.

8. A recombinant expression vector comprising the polynucleotide of claim 6.

9. A method of preparing an anti-cyanobacteria recombinant polypeptide, comprising the steps of:
transforming an E. coli with the polynucleotide of claim 6, cultivating the transformed E. coli, and separating a polypeptide expressed by the transformed *E. coli*, wherein the separated polypeptide comprises an anti-cyanobacteria recombinant polypeptide.

10. A method for controlling water eutrophication, comprising adding the anti-cyanobacteria recombinant antibody polypeptide of claim 4 to water, wherein eutrophication in the water is controlled.

11. A polynucleotide encoding the anti-cyanobacteria recombinant antibody polypeptide of claim 5.

12. A recombinant expression vector comprising the polynucleotide of claim 11.

13. A method of preparing an anti-cyanobacteria recombinant polypeptide, comprising the steps of:
   transforming an *E. coli* with the polynucleotide of claim 11,
   cultivating the transformed *E. coli*, and
   separating a polypeptide expressed by the transformed *E. coli*, wherein the separated polypeptide comprises an anti-cyanobacteria recombinant polypeptide.

14. A method for controlling water eutrophication, comprising adding the anti-cyanobacteria recombinant antibody polypeptide of claim 5 to water, wherein eutrophication in the water is controlled.

\* \* \* \* \*